US006706047B2

United States Patent
Trout et al.

(10) Patent No.: US 6,706,047 B2
(45) Date of Patent: Mar. 16, 2004

(54) SUTURE SUPPORT ASSEMBLY

(75) Inventors: Hugh H. Trout, Washington, DC (US); Howard M. Tanner, Logan, UT (US)

(73) Assignee: Eva Corporation, Bethesda, MD (US)

( * ) Notice: Subject to any disclaimer, the term of this patent is extended or adjusted under 35 U.S.C. 154(b) by 0 days.

(21) Appl. No.: 09/783,312

(22) Filed: Feb. 15, 2001

(65) Prior Publication Data

US 2001/0053924 A1 Dec. 20, 2001

Related U.S. Application Data

(60) Provisional application No. 60/182,542, filed on Feb. 15, 2000.

(51) Int. Cl.⁷ .............................................. A61B 17/10
(52) U.S. Cl. ...................................................... 606/139
(58) Field of Search ................................ 606/139, 144, 606/148, 143, 147, 232, 222, 223, 224, 225, 226, 227, 103, 104, 113

(56) References Cited

U.S. PATENT DOCUMENTS

| | | | | |
|---|---|---|---|---|
| 234,371 A | * | 11/1880 | Benjamin | 223/102 |
| 3,845,772 A | * | 11/1974 | Smith | 606/232 |
| 4,140,126 A | * | 2/1979 | Choudhury | 128/325 |
| 4,485,817 A | * | 12/1984 | Swiggett | 128/334 |
| 4,898,156 A | * | 2/1990 | Gatturna et al. | 606/72 |
| 5,002,550 A | * | 3/1991 | Li | 606/139 |
| 5,042,707 A | * | 8/1991 | Taheri | 606/213 |
| 5,192,287 A | * | 3/1993 | Fournier et al. | 606/139 |
| 5,312,438 A | * | 5/1994 | Johnson | 606/232 |
| 5,387,227 A | * | 2/1995 | Grice | 606/222 |
| 5,447,512 A | * | 9/1995 | Wilson et al. | 606/139 |
| 5,573,548 A | * | 11/1996 | Nazre et al. | 606/232 |
| 5,607,432 A | * | 3/1997 | Fucci | 606/104 |
| 5,626,614 A | * | 5/1997 | Hart | 606/232 |
| 5,632,752 A | * | 5/1997 | Buelna | 606/144 |
| 5,722,981 A | * | 3/1998 | Stevens | 606/148 |
| 5,817,112 A | * | 10/1998 | Christoudias | 606/148 |
| 5,868,789 A | * | 2/1999 | Huebner | 606/232 |
| 6,045,561 A | * | 4/2000 | Marshall et al. | 606/148 |
| 6,132,439 A | * | 10/2000 | Kontos | 606/139 |
| 6,139,556 A | * | 10/2000 | Kontos | 606/144 |
| 6,159,224 A | * | 12/2000 | Yoon | 606/147 |
| 6,217,597 B1 | * | 4/2001 | Tanner | 606/167 |
| 6,228,096 B1 | * | 5/2001 | Marchand | 606/139 |
| 6,258,106 B1 | * | 7/2001 | Leonard | 606/148 |
| 6,342,059 B1 | * | 1/2002 | Chevillon et al. | 606/139 |

* cited by examiner

Primary Examiner—John J. Calvert
Assistant Examiner—Alissa L Hoey
(74) Attorney, Agent, or Firm—Collier, Shannon, Scott, PLLC

(57) ABSTRACT

The present invention is directed to a suture support assembly for use during a surgical procedure. The suture support assembly in accordance with the present invention includes an elongated main body portion, and a proximal end portion having a passageway formed therein for receiving at least one suture therein. The proximal end portion and at least a portion of the elongated main body portion are adapted to be located within a vessel during the surgical procedure. The suture support assembly may be inserted into the vessel via an axillary incision, a brachial incision, or a femoral or a common iliac arteriotomy, and may be used in connection with the repair of an abdominal aortic aneurysm.

17 Claims, 2 Drawing Sheets

SUTURE SUPPORT ASSEMBLY

CROSS REFERENCE TO RELATED APPLICATION

The present invention relates to and claims priority on U.S. Provisional Patent Application Ser. No. 60/182,542, filed Feb. 15, 2000.

FIELD OF THE INVENTION

The present invention relates generally to a suture support device. In particular, the present invention relates to a suture support assembly for use during a surgical procedure. In particular, the present invention is directed to a suture support assembly for use in manipulating and supporting a suture within a vessel during a surgical procedure.

BACKGROUND OF THE INVENTION

An aneurysm is a ballooning of the wall of an artery resulting from the weakening of the artery due to disease or other conditions. Left untreated, the aneurysm will frequently rupture, resulting in loss of blood through the rupture and death.

Aortic aneurysms are the most common form of arterial aneurysm and are life threatening. The aorta is the main artery which supplies blood to the circulatory system. The aorta arises from the left ventricle of the heart, passes upward and bends over behind the heart, and passes down through the thorax and abdomen. Among other arterial vessels branching off the aorta along its path, the abdominal aorta supplies two side vessels to the kidneys, the renal arteries. Below the level of the renal arteries, the abdominal aorta continues to about the level of the fourth lumbar vertebrae (or the navel), where it divides into the iliac arteries. The iliac arteries, in turn, supply blood to the lower extremities and perineal region.

It is common for an aortic aneurysm to occur in that portion of the abdominal aorta between the renal arteries and the iliac arteries. This portion of the abdominal aorta is particularly susceptible to weakening, resulting in an aortic aneurysm. Such an aneurysm is often located near the iliac arteries. An aortic aneurysm larger than about 5 cm in diameter in this section of the aorta is ominous. Left untreated, the aneurysm may rupture, resulting in rapid, and usually fatal, hemorrhaging. Typically, a surgical procedure is not performed on aneurysms smaller than 5 cm because no statistical benefit exists in performing such procedures.

Aneurysms in the abdominal aorta are associated with a particularly high mortality rate; accordingly, current medical standards call for urgent operative repair. Abdominal surgery, however, results in substantial stress to the body. Although the mortality rate for an aortic aneurysm is extremely high, there is also considerable mortality and morbidity associated with open surgical intervention to repair an aortic aneurysm. This intervention involves penetrating the abdominal wall to the location of the aneurysm to reinforce or replace the diseased section of the aortic aneurysm. A prosthetic device, typically a synthetic tube graft, is used for this purpose. The graft serves to exclude the aneurysm from the circulatory system, thus relieving pressure and stress on the weakened section of the aorta at the aneurysm.

Repair of an aortic aneurysm by surgical means is a major operative procedure. Substantial morbidity accompanies the procedure, resulting in a protracted recovery period. Further, the procedure entails a substantial risk of mortality. While surgical intervention may be indicated and the surgery carries attendant risk, certain patients may not be able to tolerate the stress of intra-abdominal surgery. It is, therefore, desirable to reduce the mortality and morbidity associated with intra-abdominal surgical intervention.

In recent years, methods have been developed to attempt to treat an aortic aneurysm without the attendant risks of intra-abdominal surgical intervention. Among them are inventions disclosed and claimed in Kornberg, U.S. Pat. No. 4,562,596 for Aortic Graft, Device and Method for Performing an Intraluminal Abdominal Aortic Aneurysm Repair; Lazarus, U.S. Pat. No. 4,787,899 for Intraluminal Graft Device, System and Method; and Taheri, U.S. Pat. No. 5,042,707 for Intravascular Stapler, and Method of Operating Same.

Kornberg discloses an aortic graft comprising a flexible tubular material having a plurality of struts to lend the graft stability and resiliency. The struts have angled hooks with barbs at their upper ends which are securely attached to the inside of the aorta above the aneurysm. Kornberg's graft is inserted using a tubular device also disclosed in his patent. Kornberg, however, only anchors the proximal end of the graft. Kornberg claims that the downward flow of blood holds the distal graft securely in place, so that no mechanical attachment is necessary distally. The blood pressure in the abdominal aorta, however, is typically in the magnitude of 130 mm of mercury (Hg). In spite of the direction of flow of blood through the graft, proximal to distal, substantial back pressure within the aneurysm will result unless the distal end is also mechanically attached to the aorta in a manner that prevents substantial leakage of blood between the graft and the aorta. Without distal attachment, the device of Kornberg will not effectively exclude the weakened arterial wall at the site of the aneurysm from the forces and stress associated with the blood pressure.

Lazarus discloses a grafting system that employs a plurality of staples mounted in the proximal end of the graft. Lazarus's staples are forced through the aorta wall by means of a balloon catheter. As does Kornberg, Lazarus discloses staples mounted only in the proximal end of the graft. There is no teaching or suggestion in Lazarus, U.S. Pat. No. 4,787,899 as to the desirability of, let alone means for, mechanically attaching the graft to the distal aorta below the level of the aneurysm.

Taheri discloses an articulatable stapler for implanting a graft in a blood vessel. The stapler is in the form of an elongated catheter with a plurality of segments mounted on the distal end of the catheter. The segments have beveled faces and are connected to each other by hinges. A stylet runs through the catheter to the most distal segment. The most distal segment is moved, in conjunction with the other segments, into a firing position that is substantially perpendicular to the main catheter body by the action of pulling on the stylet. The staple is implanted by using two other stylets which act as fingers to bend the staple into its attachment position.

Taheri, however, appears to be a single-fire design which can only implant one staple at a time. After each stapler is implanted, Taheri's design apparently requires that the catheter be removed before another staple is loaded. In addition, Taheri's does not teach or suggest an appropriate density of staples to secure a graft against the pulsatile blood flow of the aorta. Pressures within the aorta range from 120 mm Hg pressure to 200 mm Hg pressure. Without adequate attachment, the graft may leak around the edges continuing to allow life threatening pressures to develop in the aneurysm, and may not even remain in place.

During a surgical procedure a suture normally may be used to attach a surgical component to a vessel. An apparatus is not currently known that can support a suture within a vessel during a surgical procedure with the advantages of the present invention. Fraying of the suture during a surgical procedure is also an ongoing problem. Another problem that faces the physician is that the suture may become entangled with other surgical components during the procedure. It would also be useful if an apparatus as described above could assist in temporarily supporting a surgical component within the vessel while the surgical component is being permanently affixed to the vessel.

OBJECTS OF THE INVENTION

It is an object of the present invention to provide an assembly for supporting a suture within a vessel during a surgical procedure.

It is another object of the present invention to provide a suture support assembly for use during a surgical procedure that minimizes fraying of the suture.

It is another object of the present invention to provide a suture support assembly for use during a surgical procedure that prevents the suture from being entangled with other surgical components.

It is another object of the present invention to provide a suture support assembly that assists in temporarily supporting a graft assembly within a vessel while the graft assembly is being permanently affixed to the vessel.

SUMMARY OF THE INVENTION

The present invention is directed to a suture support assembly for use during a surgical procedure. The suture support assembly in accordance with the present invention includes an elongated main body portion, and a proximal end portion having a passageway formed therein for receiving at least one suture therein. The proximal end portion and at least a portion of the elongated main body portion are adapted to be located within a vessel during the surgical procedure. The suture support assembly may be inserted into the vessel via an axillary incision, a brachial incision, or a femoral or a common iliac arteriotomy, and may be used in connection with the repair of an abdominal aortic aneurysm.

The first end of the passageway terminates at a free end portion of the proximal end portion. The free end portion of the proximal end portion includes rounded edges. A second end of the passageway terminates at an opening in the proximal end portion, wherein the opening is located at an opposite end from the free end portion of the proximal end portion.

According to an embodiment of the present invention, the opening at the opposite end of the proximal end portion is located at a point sufficiently below a location where the surgical procedure is being performed. The interior of the proximal end portion may include an angled surface adjacent to the opening which directs the suture toward the opening.

According to an embodiment of the present invention, the suture support assembly may be used to support a graft assembly during a surgical procedure. At least one suture and at least one suture support assembly may be used in combination to support the surgical component in a desired location within the vessel. A separator assembly may also be used in connection with the suture and the suture support assembly.

It is to be understood that both the foregoing general description and the following detailed description are exemplary and explanatory only, and are not restrictive of the invention, as claimed. The accompanying drawings, which are incorporated herein by reference, and which constitute a part of this specification, illustrate certain embodiments of the invention, and together with the detailed description serve to explain the principles of the present invention.

BRIEF DESCRIPTION OF THE DRAWINGS

The invention will be described in conjunction with the following drawing in which like reference numerals designate like elements and wherein.

DETAILED DESCRIPTION OF PREFERRED EMBODIMENTS

Figure 1:
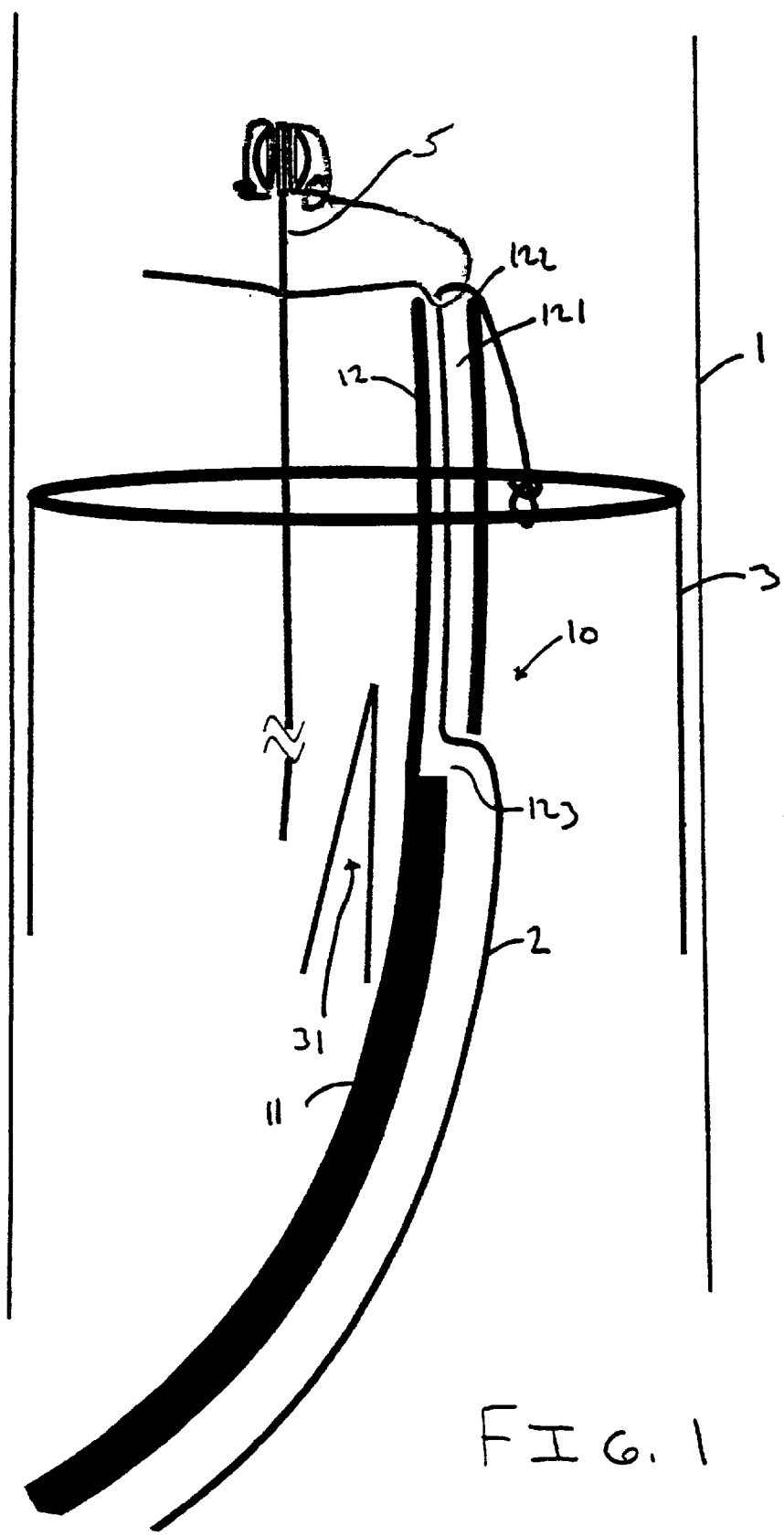
FIG. 1 is a schematic view of a suture support assembly in accordance with the present invention for use during a surgical procedure.
Figure 2:
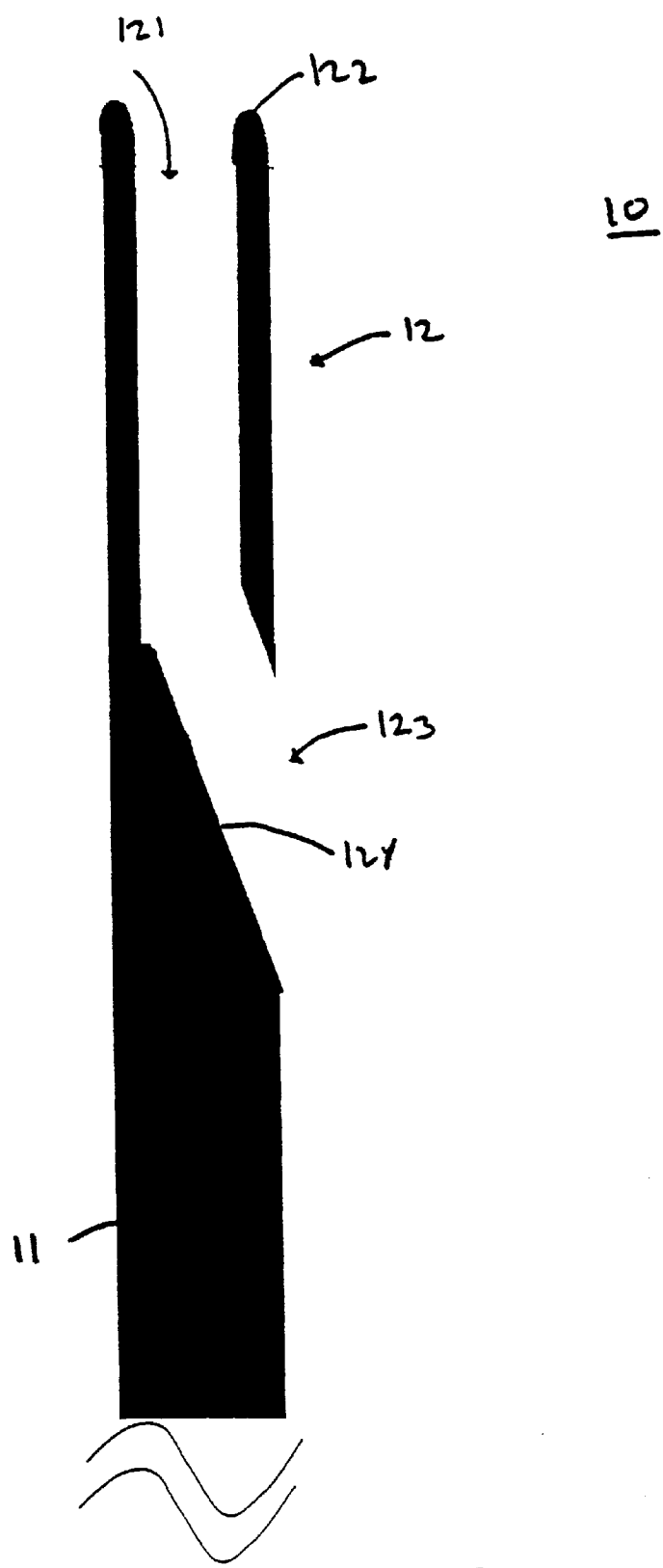
FIG. 2 is an enlarged schematic view of the tip of the suture support assembly of FIG. 1.

A suture support assembly 10 in accordance with the present invention is disclosed in FIGS. 1 and 2. The suture support assembly 10 includes a main body portion 11 and a proximal end portion 12. The proximal end portion 12 and at least a portion of the main body portion 11 are adapted to be located within a vessel 1 during a surgical procedure. It is contemplated that the suture support assembly 10 in accordance with the present invention is used in connection with repair of an abdominal aortic aneurysm. The present invention, however, is not limited to solely to the repair of aneurysms; rather, it is contemplated that the present invention may be used in connection with any one of numerous surgical procedures during which sutures or other surgical devices are used within a vessel 1. The main body portion 11 of the suture support assembly 10 has sufficient length such that it may extend from either an axillary incision, a brachial incision or a femoral or common iliac arteriotomy to the procedure specific area within the vessel 1.

The main body portion 11 is preferably has a solid construction and may be formed, for example, from a solid reasonably stiff guide line. It, however, is contemplated that the main body portion 11 may have a hollow configuration so long as it may be supported from outside the patient and will not bend appreciably in the face of brisk arterial blood flow.

The proximal end portion 12 has a hollow configuration, as shown, for example, in FIGS. 1 and 2 to permit the insertion of a suture 2 therein. The proximal end portion 12 includes a central passageway 121 extending therein. The passageway 121 terminates at the free end portion 122 of the proximal end portion 12. The free end portion 122 preferably includes rounded edges, as shown in FIG. 2 to prevent the fraying of a suture 2 located therein. An opposite end of the proximal end portion 12 includes an opening 123 therein through which the suture 3 may exit. The proximal end portion 12 should have sufficient length such that the opening 123 is located at a point sufficiently below the location where a surgical procedure is being performed (e.g., the location at which a graft assembly 3 is secured to a vessel 1) so that risk of the suture 2 snagging on one of the surgical components located within the vessel 1 is minimized. This is especially important upon completion of the surgical procedure (i.e., after the graft assembly 3 has been secured to the vessel 1) such that the sutures 2 do not become entangled with a surgical component and/or fastener which may result in the unintentional separation of the graft assembly 3 and the vessel 1. In FIG. 1, the graft assembly 3 is a bifurcated graft having a bifurcation 31, the opening 123 is preferably located below the bifurcation 31.

The interior of the proximal end portion 12 adjacent opening 123 may include an angled surface 124 to direct the suture 2 toward the opening 123, as shown in FIG. 2.

In accordance with the present invention, the suture support assembly 10 is used to support a graft assembly 3 during a surgical procedure. In particular, the suture 2 and suture support assembly 10 are use in combination to support a graft assembly 3 in a desired location within the vessel 1. One or more suture support assemblies 10 may be used to perform this function while the graft assembly 3 is being permanently secured to the vessel 1. Furthermore, the suture 2 and suture support assembly 10 may be used in connection with separator assembly 5, as disclosed in PCT International Application No. PCT/US00/03871 entitled "SURGICAL GUIDE LINE ASSEMBLY AND SEPARATOR ASSEMBLY FOR USE DURING A SURGICAL PROCEDURE," filed on Feb. 4, 2000, the disclosure of which is incorporated herein specifically by reference. The separator assembly 5 may be used to position and rotate a graft assembly 3 within the vessel 1.

It will be apparent to those skilled in the arts that various modifications and variations can be made in the construction and configuration of the present invention, without departing from the scope or spirit of the invention. It is intended that the present invention cover the modifications and variations of the invention, provided they come within the scope of the appended claims and their equivalence.

What is claimed is:

1. A suture support assembly for use during a surgical procedure, said suture assembly comprising:
    an elongated main body having a proximal end and a distal end; and
    the proximal end having a hollow passageway formed therein for receiving a suture therein, the hollow passageway extending from a free end portion located at the proximal end to an opening located opposite to the free end portion positioned below the surgical procedure and above the distal end.

2. The suture support assembly according to claim 1, wherein said proximal end portion and at least a portion of said elongated main body portion are adapted to be located within a vessel during the surgical procedure.

3. The suture support assembly according to claim 2, wherein said suture support assembly is inserted into the vessel via an axillary incision, a brachial incision, or a femoral or a common iliac arteriotomy.

4. The suture support assembly according to claim 1, wherein said suture support assembly is used in connection with the repair of an abdominal aortic aneurysm.

5. The suture support assembly according to claim 1, wherein a first end of said passageway terminates at a free end portion of said proximal end portion.

6. The suture support assembly according to claim 5, wherein said free end portion of said proximal end portion includes rounded edges.

7. The suture support assembly according to claim 5, wherein a second end of said passageway terminates at an opening in said proximal end portion, wherein said opening is located at an opposite end from said free end portion of said proximal end portion.

8. The suture support assembly according to claim 7, wherein said opening at said opposite end of said proximal end portion is located at a point sufficiently below a location where said surgical procedure is being performed.

9. The suture support assembly according to claim 7, wherein the interior of said proximal end portion includes an angled surface adjacent to said opening which directs said at least one suture toward said opening.

10. The suture support assembly according to claim 1, wherein said suture support assembly is used to support a surgical component during a surgical procedure.

11. The suture support assembly according to claim 10, wherein said at least one suture and at least one suture support assembly are used in combination to support said surgical component in a desired location within the vessel.

12. The suture support assembly according to claim 11, wherein a separator assembly is used in connection with said at least one suture and said at least one suture support assembly.

13. A suture support assembly for use during a surgical procedure comprising:
    a solid elongated body having a proximal end and a distal end, the proximal end having a hollow passageway extending from a free end portion located at the proximal end to an opening located opposite to the free end portion positioned below the surgical procedure and above the distal end, wherein the hollow passageway accommodates a suture.

14. The suture support assembly of claim 13, wherein the free end portion has rounded edges.

15. The suture support assembly of claim 13, wherein the proximal end of the elongated body is adapted to be located within a vessel during the surgical procedure.

16. The suture support assembly of claim 13, wherein the suture support assembly is used in connection with the repair of an abdominal aortic aneurysm.

17. The suture support assembly of claim 13, wherein the second opening is angled to direct the suture toward the free end portion.

* * * * *